United States Patent
Van Tilborg

(10) Patent No.: US 10,434,049 B2
(45) Date of Patent: *Oct. 8, 2019

(54) METHODS OF PRODUCING COMPOUNDS THAT STIMULATE HAIR REGROWTH, TOPICAL FORMULATIONS, AND METHODS OF USE

(71) Applicant: Joventis S.A., Strassen (LU)

(72) Inventor: Reiner Van Tilborg, Strassen (LU)

(73) Assignee: Joventis, S.A., Strassen (LU)

( * ) Notice: Subject to any disclaimer, the term of this patent is extended or adjusted under 35 U.S.C. 154(b) by 0 days.

This patent is subject to a terminal disclaimer.

(21) Appl. No.: 15/163,555

(22) Filed: May 24, 2016

(65) Prior Publication Data

US 2016/0262995 A1 Sep. 15, 2016

Related U.S. Application Data

(63) Continuation-in-part of application No. 14/917,941, filed as application No. PCT/EP2014/069424 on Sep. 11, 2014.

(30) Foreign Application Priority Data

Sep. 11, 2013 (LU) .......................................... 92277

(51) Int. Cl.
| | |
|---|---|
| *A61K 8/31* | (2006.01) |
| *C07C 2/86* | (2006.01) |
| *A61Q 19/00* | (2006.01) |
| *A61Q 7/00* | (2006.01) |
| *A61K 8/11* | (2006.01) |
| *C07C 13/39* | (2006.01) |
| *C07C 13/44* | (2006.01) |

(52) U.S. Cl.
CPC .................. *A61K 8/31* (2013.01); *A61Q 7/00* (2013.01); *C07C 13/39* (2013.01); *C07C 13/44* (2013.01); *C07C 2602/06* (2017.05); *C07C 2602/20* (2017.05); *C07C 2602/42* (2017.05)

(58) Field of Classification Search
CPC .. A61K 8/31; A61Q 7/00; C07C 13/39; C07C 13/44; C07C 2602/06; C07C 2602/20; C07C 2602/42
See application file for complete search history.

(56) References Cited

U.S. PATENT DOCUMENTS 2,794,822 A * 6/1957 Schweitzer ............. C07C 45/46
12/136 R

OTHER PUBLICATIONS

Clinical trial: retrieved from internet: http://joventis.com/en/index.html under "Clinical Trial". Retrieved on Nov. 23, 2016.*
Conference: retrieved from internet: http://joventis.com/en/index.html under "Conferences". Retrieved on Nov. 23, 2016.*
http://www.adichemistry.com/organic/namedreactions/friedelcrafts/friedel-crafts-alkylation-1.html. Retrieved on Aug. 18, 2017.*

* cited by examiner

*Primary Examiner* — Hong Yu
(74) *Attorney, Agent, or Firm* — Umberg Zipser LLP

(57) ABSTRACT

A method performing a Friedel-Crafts alkylation reaction between a dichloroalkane and an alkylbenzene produces a compound for hair regrowth. The inventive subject matter further includes incorporation of such compounds in topical formulations with suitable carriers. The resulting topical formulations may be employed in methods of stimulating hair regrowth.

17 Claims, 8 Drawing Sheets

METHODS OF PRODUCING COMPOUNDS THAT STIMULATE HAIR REGROWTH, TOPICAL FORMULATIONS, AND METHODS OF USE

This application is a continuation-in-part of U.S. patent application Ser. No. 14/917,941 (filed Mar. 9, 2016), which is the national phase application of PCT/EP2014/069424 (filed Sep. 11, 2014), which claims priority to Luxembourg Patent Application No. LU92277 (filed Sep. 11, 2013). The subject matter disclosed in these documents is incorporated herein in their entirety.

FIELD OF THE INVENTION

The field of the invention is methods of producing compounds that stimulate hair regrowth, topical formulations comprising hair regrowth stimulating compounds, and methods of stimulating hair regrowth by applying the topical formulations.

BACKGROUND

The following background discussion includes information that may be useful in understanding the present invention. It is not an admission that any of the information provided herein is prior art or relevant to the presently claimed invention, or that any publication specifically or implicitly referenced is prior art. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

U.S. Patent Pub. No. 2015/0314044 to Gho (filed Dec. 12, 2013) discloses significantly improved hair transplantation methods that provide greater hair density per hair implant, which is achieved through the process of an enhanced hair multiplication in vivo (e.g. in the scalp of a subject). Gho's methods are particularly suitable for hair transplantation in areas of a subject where there is baldness or lack of hair, such as caused by Androgenic alopecia, burn injuries, cancer chemotherapy, or other genetic or environmental factors or scarring. However, Gho fails to appreciate that surgical hair transplantation is invasive and that topical compositions are preferable to many potential patients. Therefore, there is still a need for methods that produce compounds that stimulate hair regrowth, associated topical compositions, and their methods of use.

SUMMARY OF THE INVENTION

The inventive subject matter provides methods in which one can produce a compound for hair regrowth. The method comprises steps of: (1) adding a Friedel-Crafts catalyst to a dichloroalkane to generate a first intermediate at a first temperature; (2) adding the first intermediate to an alkylbenzene at the first temperature and to generate a second intermediate; (3) cooling the second intermediate to a second temperature to generate a third intermediate; (4) incubating the third intermediate at the second temperature for a first duration; (5) warming the third intermediate to a third temperature and incubating the third intermediate at the third temperature for a second duration; (6) cooling the third intermediate to the second temperature and incubating the third intermediate at the second temperature for a third duration; and (7) repeating steps (5) and (6) at least four times.

One having ordinary skill in the art would appreciate that suitable Friedel-Crafts catalysts include aluminum trichloride and ferric chloride. Additionally, dichloroalkane preferably comprises 1,2-dichloropropane. Moreover, preferred alkyl benzenes comprise toluene.

In regard to the first, second and third temperatures, in exemplary embodiments of the inventive methods, the first temperature is between −10 and 15 degrees Celsius, inclusive, the second temperature is between −90 and −70 degrees Celsius, inclusive, and the third temperature is between 30 and 50 degrees Celsius, inclusive. Preferably, the first temperature is about, the second temperature is about, and the third temperature is about 40 degrees Celsius.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In yet further exemplary embodiments of the inventive methods, the first, second, and third duration are about 30 minutes.

Therefore, it should be appreciated that the compounds produced by the inventive methods may be combined with a carrier to make a topical formulation for stimulating hair regrowth. The inventors contemplate topical formulations comprising compounds having a molecular formula of $C_{13}H_{20}$. Further, the inventors contemplate that the compound's structure may comprise a bicycloheptane. More generally, the inventors contemplate that compounds consistent with the inventive subject matter comprises a dialkylbenzene or a trialkylbenzene.

The topical formulations may be formulated as creams, lotions, ointments, sprays, foams, or gels. Suitable formulations may further incorporate the inventive compounds in the form of micelles, liposomes, or polymer beads that encapsulate the compounds for hair regrowth.

In yet further aspects of the inventive subject matter, a method of stimulating hair regrowth comprises: (1) providing a topical formulation according to the inventive subject matter in an amount effective to stimulate at least one of: activate the anagen phase in a hair follicle; inhibit the hair follicle from entering the catagen phase; revert the hair follicle from the catagen phase to the anagen phase; and promoting the hair follicle to enter the anagen phase from the telogen phase; and (2) applying the topical formulation to a treatment area of a human in need thereof. Without wishing to be bound by a particular theory, the inventors hypothesize that such effects may arise from stimulation of expression of Lgr5 in a follicular stem cell in the treatment area of the human in need thereof. Such methods may be particularly advantageous in cases where the treatment area comprises an injured site, especially a burn (caused by heat, chemical, cold, etc.).

Various objects, features, aspects and advantages of the inventive subject matter will become more apparent from the following detailed description of preferred embodiments, along with the accompanying drawing figures in which like numerals represent like components.

DETAILED DESCRIPTION

The inventive subject matter provides methods in which one can produce a compound for hair regrowth, topical formulations that incorporate the compound for hair regrowth, and methods of stimulating hair regrowth using the topical formulations. A preferred method comprises steps of: (1) adding a Friedel-Crafts catalyst to a dichloroalkane to generate a first intermediate at a first temperature; (2) adding the first intermediate to an alkylbenzene at the first temperature and to generate a second intermediate; (3) cooling the second intermediate to a second temperature to generate a third intermediate; (4) incubating the third intermediate at the second temperature for a first duration; (5) warming the third intermediate to a third temperature and incubating the third intermediate at the third temperature for a second duration; (6) cooling the third intermediate to the second temperature and incubating the third intermediate at the second temperature for a third duration; and (7) repeating steps (5) and (6) at least four times.

For example, methods consistent with the inventive subject matter include reactions according to Scheme 1 in which an alkylbenzene reacts with a 1,2-dichloroalkane in the presence of a Friedel-Crafts catalyst. In suitable alkylbenzenes, the R group may comprise methyl, ethyl, propyl, isopropyl, n-butyl, i-butyl, t-butyl, n-pentyl, i-pentyl, longer n-alkyl, or longer, branched alkyl groups. An especially preferred alkyl benzene comprises toluene. Without wishing to be bound by a particular hypothesis, the inventors contemplate that each alkylbenzene undergoes two Friedel-Crafts alkylations and further transformations to form bicyclo[3.1.1]hepta-2,4-diene and/or bicyclo[4.1.0]hepta-2,4-dienes, wherein the alk-2-yl moiety may be bound to either of the bridgehead carbons in the bicyclo[4.1.0]hepta-2,4-dienes.

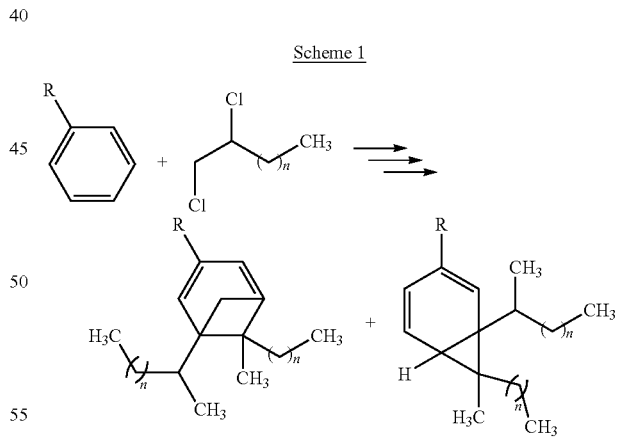

Scheme 1

Figure 1:
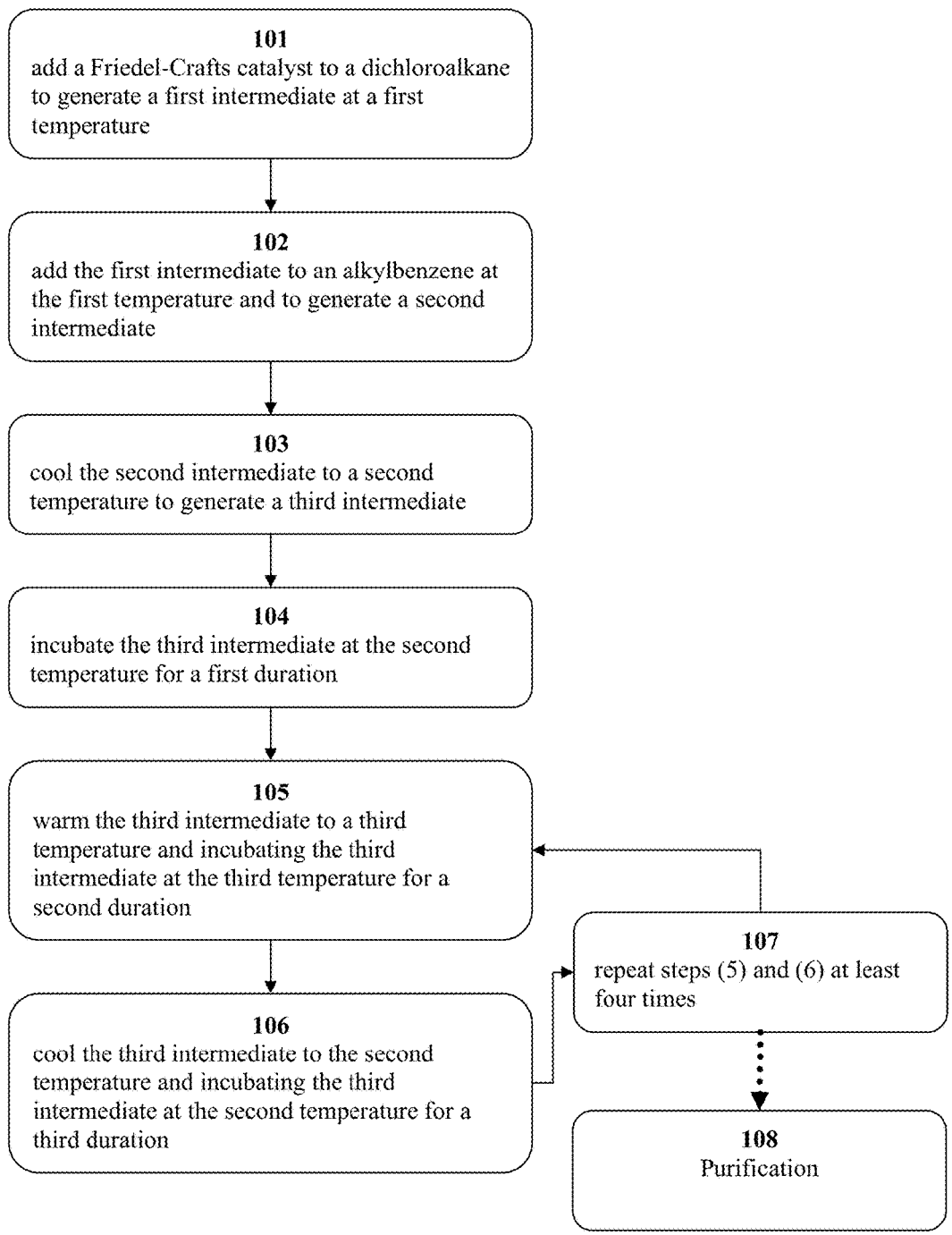
FIG. 1 shows a flow diagram of a method of producing a compound for stimulating hair regrowth.
Figure 2A:
FIG. 2A shows a balding male with a complete bald spot and very thin grey hair before treatment.
Figure 2B:
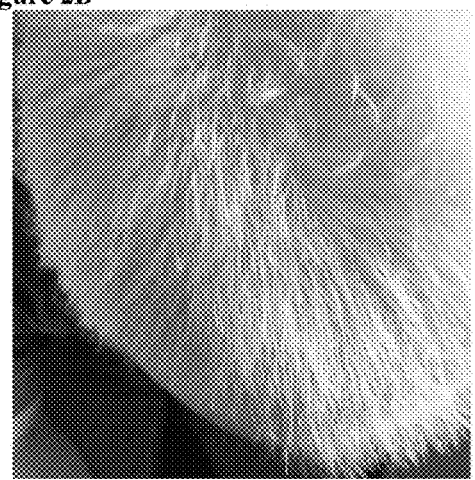
FIG. 2B shows hair growth on the subject from FIG. 2A after 6 months of treatment with the compound of Formula (I).
Figure 2C:
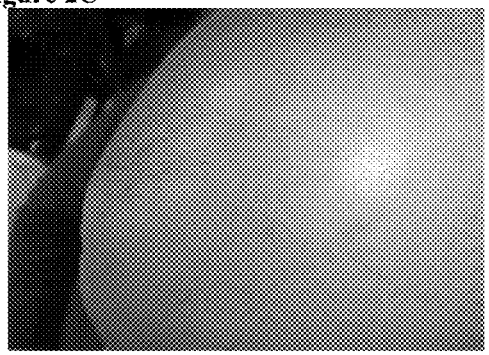
FIG. 2C shows a balding male before treatment.
Figure 2D:
FIG. 2D shows hair growth on the subject from FIG. 2C after 6 months of treatment with the compound of Formula (I).

FIG. 1 shows a flow chart of a preferred method. In step 101, adding a Friedel-Crafts catalyst to generate a first intermediate at a first temperature, one having ordinary skill in the art would appreciate that suitable Friedel-Crafts catalysts include aluminum trichloride, ferric chloride, boron trifluoride, zinc chloride, aluminum tribromide, and ferric bromide. Additionally, dichloroalkane may comprise 1,2-dichloroalkanes, 1,1-dichloroalkanes, or 2,2-dichloroalkanes. Contemplates dichloroalkanes include dichloromethane, dichloroethanes, dichloropropanes, dichlorobutanes, dichloropentanes, dichlorohexanes etc. The inventors contemplate use of both linear and branched dichloroalkanes in the inventive methods. In especially preferred embodiments, the dichloroalkane comprises 1,2-dichloropropane.

One having ordinary skill in the art would further appreciate that the first intermediate comprises a carbocation and a Friedel-Crafts catalyst chloride (e.g., $AlCl_4^-$). Although both primary and secondary carbocations may be formed from 1,2-dichloroalkanes, primary carbocations may undergo hydride shifts to form the corresponding secondary carbocation. Thus, the inventors contemplate that secondary carbocations predominate in the first intermediate.

In regard to the first, second and third temperatures, in exemplary embodiments of the inventive methods, the first temperature is between −10 and 15 degrees Celsius, inclusive. Preferably the first temperature is about 4 degrees Celsius. The second temperature is preferably between −90 and −70 degrees Celsius, inclusive, and even more preferably, about −80 degrees Celsius. The third temperature is preferably between 30 and 50 degrees Celsius, inclusive. Preferably, the third temperature is about 40 degrees Celsius.

In yet further exemplary embodiments of the inventive methods, the first, second, and third duration are about 30 minutes. Moreover, step (3) cooling the second intermediate to the second temperature preferably takes one minute or less.

In regard to step 102, the first intermediate is added to the alkyl benzene at the first temperature (e.g., −10 and 15 degrees Celsius, preferably about 4 degrees Celsius) to generate a second intermediate. The second intermediate may comprise a disubstituted alkylbenzene, wherein the first intermediate adds to the alkylbenzene para to the R-group (major product) or ortho to the R-group (minor product), because alkyl substitutents are mildy electron donating ortho para directors.

In step 103, the second intermediate is cooled to a second temperature (e.g., −90 to −70 degrees Celsius, preferably −80 degrees Celsius) to generate a third intermediate. Step 104 comprises incubating the third intermediate at the second temperature for a first duration (about 30 minutes).

Next step 105, the third intermediate is warmed to a third temperature (e.g., 30-50 degrees Celsius, preferably about 40 degrees Celsius) and incubated the third intermediate at the third temperature for a third duration (about 30 minutes). Step 106 includes cooling the third intermediate to the second temperature (e.g., −90 to −70 degrees Celsius, preferably −80 degrees Celsius) and incubating the third intermediate at the second temperature for a third duration (about 30 minutes).

In step 107, steps 105 and 106 are repeated at least four times. Optionally, a purification step 108 may be used to remove the Friedel-Crafts catalyst, unreacted reagents, and/or any minor side-products of reaction. For example Friedel-Crafts catalysts may be removed by aqueous extraction. Other components may be removed by distillation, crystallization, chromatography, etc.

A preferred method of producing a compound for hair regrowth is shown in Scheme 2, and comprises, adding aluminum trichloride to a 1,2-dichloropropane at about 4 degrees Celsius to generate a first intermediate (a carbocation and alumininum tetrachloride). Step (2) comprises adding the first intermediate to toluene at about 4 degrees Celsius to generate a second intermediate, and in a minute or less proceeding through Step (3). Step (3) comprises cooling the second intermediate to about −80 degrees Celsius to generate a third intermediate. Next Step (4), comprises incubating the third intermediate at about −80 degrees Celsius for about 30 minutes. Step (5) comprises warming the third intermediate to about 40 degrees Celsius and incubating the third intermediate for about 30 minutes. Step (6) comprises cooling the third intermediate back to −80 degrees Celsius and incubating the third intermediate at −80 degrees Celsius for about 30 minutes. Finally, Step (7) comprises repeating steps (5) and (6) at least four times. One having ordinary skill in the art appreciates that the compound may be isolated from the Friedel-Crafts catalyst, the reagents, and any other contaminants using conventional purification techniques (e.g., maceration, extraction, chromatography, distillation, crystallization, etc.)

Without wishing to be bound by a particular hypothesis, the inventors contemplate that methods according to the inventive subject matter first produce a mono-alkylated product, e.g., 1-(1-chloropropan-2-yl)-4-methylbenzene (Scheme 2). After a second alkylation and further reaction, the inventors hypothesize that the inventive methods yield compounds having a molecular formula of $C_{13}H_{20}$. Further, the inventors contemplate that the compound's structure may comprise a bicycle[3.1.1]heap-1,3-diene or a bicyclo[4.1.0]hepta-2,4-diene.

For example, preferred methods may yield one or more of 3,6,6-trimethyl-5-(propan-2-yl)bicyclo[3.1.1]hepta-1,3-diene(Formula (I)/JR101s); 3,7,7-trimethyl-1-(propan-2-yl)bicyclo[4.1.0]hepta-2,4-diene (Formula (II)); 4,7,7-trimethyl-1-(propan-2-yl)bicyclo[4.1.0]hepta-2,4-diene, or other products.

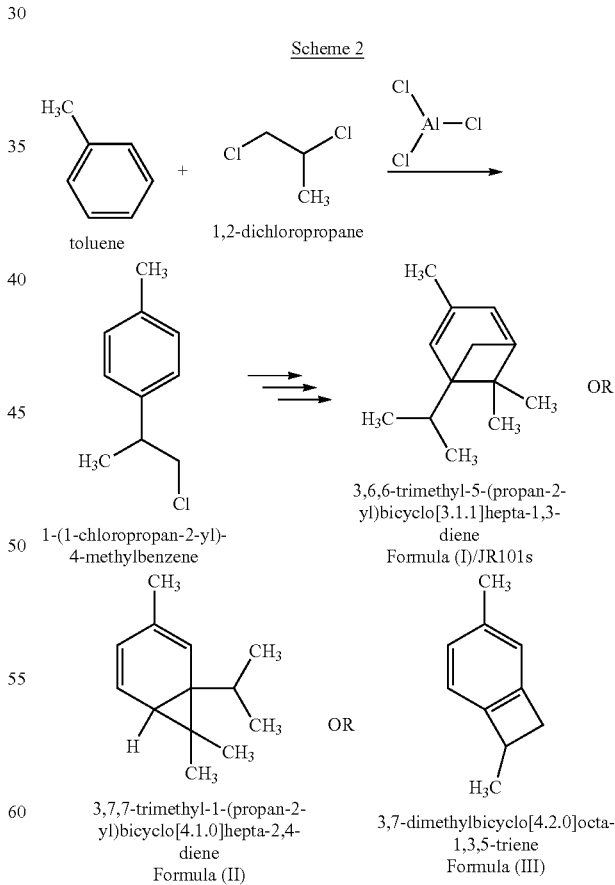

Scheme 2

Compounds consistent with the inventive subject matter may further comprise 3,7-dimethylbicyclo[4.2.0]octa-1,3,5-triene (Formula (III)). Additionally, trialkylbenzenes and extended chains of linked alkylbenzenes are not excluded. Moreover, contemplated compounds may comprise one or more chlorine atoms.

Such compounds produced by the inventive methods may be combined with a carrier to make topical formulations for stimulating hair regrowth. The topical formulations may be formulated as creams, lotions, ointments, sprays, foams, or gels. Aloe vera is contemplated for use as a base in gel formulations. Additionally, aloe powder may be incorporated into creams and lotions. Suitable formulations may further incorporate the inventive compounds in the form of micelles, liposomes, nanoparticles, proteins, or polymer beads that encapsulate the compounds for hair regrowth.

In still further contemplated aspects, the compounds for stimulating hair regrowth can be encapsulated in cosmetically acceptable formulations, and especially formulations using a lipid membrane. For example, micelles, liposomes, microcapsules, nanocapsules, microparticles, nanoparticles, microparticle delivery systems, are especially contemplated. A description of some cosmetically acceptable cosmetic delivery systems can be found in Maherani et al, "Liposomes: A Review of Manufacturing Techniques and Targeting Strategy," Current Nanoscience; 7:436-452 (2011). A preferred method of liposome manufacturing is a shear method. Preferred cosmetic delivery systems resemble naturally occurring membranes, are flexible, and can penetrate interstitial spaces between cells. It is further contemplated that cosmetic delivery systems may have monolayer, bilayer (e.g. unilammellar vesicle or ULV), or multi layer structures (e.g. multilamellar vesicle or MLV). Additionally, multilayer liposomes, microcapsules, microsomes, and nanocapsules can have nested structures (e.g. multivesicular vesicle or MVV). Cosmetic delivery systems used in the topical formulations can range in size from about 500 nm to about 10 μm. In the preparation of cosmetic delivery systems, all cosmetically acceptable lipid compositions are contemplated, especially pharmaceutically acceptable lipids. In most instances preferred cosmetic delivery systems comprise amphipathic or amphiphilic molecules such as phospholipids or combinations of phospholipids (e.g., phosphatidylcholine, phosphatidylethanolamine, phosphatidic acid, phosphatidylserine, and phosphoinositides). Additionally, in some instances contemplated cosmetic delivery systems can contain additive(s) such as sterols, polyethylene glycol, cholesterol, dicethylphosphate, stearyl amine, etc. Unilamellar vesicles/liposomes can be produced using high shear techniques.

With respect to the amount of delivery systems incorporated in each topical formulation, the cosmetic delivery system content will typically be adjusted such that when the topical formulation is applied to a treatment area of a human in need thereof, the amount of compound for stimulating hair regrowth is present in an amount effective to achieve at least one of: (i) activating the anagen phase in a hair follicle; (ii) inhibiting the hair follicle from entering the catagen phase; (iii) reverting the hair follicle from the catagen phase to the anagen phase; and (iv) promoting the hair follicle to enter the anagen phase from the telogen phase.

The inventors contemplate polymer beads, such as polystyrene beads, may serve as suitable encapsulating agents. For example, Dow® SUNSPHERES™, hollow polystyrene beads produced by inverse emulsion polymerization may be used to encapsulate the inventive compounds. The resulting polymer beads may then be incorporated into topical formulations consistent with the inventive subject matter. It should be appreciated that encapsulation of the hydrophobic compounds produced by the inventive methods increases the amount of compound that can be incorporated in aqueous topical formulations. Advantageously, Dow® SUNSPHERES™ also boost UV protection. One function of hair is to prevent sun damage to the underlying skin. Thus, applying formulations with UV protection may prevent sun damage to the treated skin until hair regrowth is sufficient to provide such protection.

In regard to suitable carriers, the inventors contemplate that creams, lotions, ointments, and sprays may be based on natural or synthetic oils. Suitable natural oils include beeswax, apricot kernel oil, avocado oil, castor oil, coconut oil, grapeseed oil, rosehip oil, sweet almond oil, sunflower oil, borage oil, camellia oil, cocoa butter, evening primrose oil, hazelnut oil, hempseed oil, macadamia oil, sesame oil, tamanu oil, and wheat germ oil. Preferred natural oils include olive oil and jojoba oil. It should be appreciated that oil bases may be prepared by blending palmitic acid, palmitoleic acid, erucic acid, eicosenoic acid, docosenoic acid, oleic acid and/or linoleic acid to achieve the desired moisturizing and healing properties. Advantageously blending fatty acid carriers is that potential allergic reactions to natural oil components are avoided.

Suitable synthetic oils comprise cosmetic and pharmaceutical grade silicone and olefin-derived oils. For example, mineral oils, dimethicones, and cyclomethicones may serve as carriers in contemplated topical formulations.

The inventors contemplate that the product(s) of the inventive methods may be incorporated in stock solutions. For example, the ratio of compound produced by the inventive processes to carrier may be 1:100, 1:50, 1:20, 1:10, 1:5, 1:2, 1:1, 2:1, 5:1, or 10:1 by weight. In one example, a 1:100 dilution of the compound is formulated by preparing a homogenous solution of 40 mL (Formula (I)) in 4 L of carrier (e.g., jojoba or olive oil).

Topical formulations may further comprise other components including water, emulsifiers, etc. Suitable emulsifiers include, but are not limited to: Borax with Beeswax, Beeswax, BTMS 25%, Carbomer, Cetaryl Alcohol, Emulsifying Wax-NF, Lecithin, PEG-20 Stearate, Propylene Glycol, Silky Emulsifying Wax, Stearyl Alcohol NF, and Polysorbate 80. Exemplary cream formulations:

| Component | Weight % | Preferred Component | Preferred Weight % |
|---|---|---|---|
| Water | 0-99.9 | Water | 57 |
| Compound produced by the inventive process | 0.1-99.9 | Formula (I) | 13 |
| Carrier | 0-99.9 | Jojoba or olive oil | 7 |
| Emulsifier | 0-50 | Tefose ® 2000 | 3 |
| Other | 0-99.9 | Propylene glycol | 20 |
| | | Total | 100 |

In yet further aspects of the inventive subject matter, a method of stimulating hair regrowth comprises: (1) providing a topical formulation of claim 9 in an amount effective to stimulate at least one of: activate the anagen phase in a hair follicle; inhibit the hair follicle from entering the catagen phase; revert the hair follicle from the catagen phase to the anagen phase; and promoting the hair follicle to enter the anagen phase from the telogen phase; and (2) applying the topical formulation to a treatment area of a human in need thereof. Without wishing to be bound by a particular theory, the inventors hypothesize that such effects may arise from stimulation of expression of Lgr5 in a follicular stem cell in the treatment area of the human in need thereof. Such methods may be particularly advantageous in cases where the treatment area comprises an injured site, especially a burn (caused by heat, chemical, cold, etc.).

FIG. 2 shows the top of two participants' heads before and after treatment with Formula (I). The subject in FIG. 2A starts out with a complete bald spot. After 6 months of treatment with Formula (I), white hair has grown into the bald spot (FIG. 2B). Before treatment with Formula (I), the subject shown in FIG. 2C has dark, balding hair. After 6 months of treatment, dark hair has begun to regrow on this subject's scalp (FIG. 2D).

In a systematic study of twenty volunteers, including 8 women, study participants self-reported hair regrowth metrics by answering questionnaires at the end of each month of treatment with Formula (I) over the course of six months. The mean age of participants was 54 years old (SD=11 years). Participants had no history of hair implants and had normal eating and sleeping patterns.

Participants first read and signed an informed consent form in which they were informed about the hair regeneration product, a lotion comprising Formula (I). The information about Formula (I) included that Formula (I) was designed to increase hair growth, that it was based on natural compounds, and that use of the product would not lead to harmful effects. Participants received explicit instructions on how to use the product, were asked to apply the product at least once a day on their scalp, and were asked not to use any other hair growth or regeneration products for the 6-month duration of the study.

In order to measure hair growth, hair thickness and color regeneration participants had a monthly session to monitor their progress. During this session photos were taken to measure and count any increases in hair regrowth, and participants answered questionnaires that probed the effects using Formula (I).

Questionnaires comprised 14 yes or no questions based on Barber's 1998 the hair growth questionnaire. Barber et al., *A hair growth questionnaire for use in the evaluation of therapeutic effects in men*, J. DERMATOLOGICAL TREATMENT, Vol. 9(3), pp. 181-86 (1998). The questions included:

Did you notice new hair growth during the past month?
Did you notice new hair growth since the start of treatment?
Did you notice any new hair loss during the past month?
Did you notice any new hair loss since the start of the treatment?
Did you notice more hair loss than before since the start of the treatment?
Did you notice that your hairs felt thicker during the past month?
Did you notice that your hairs felt thicker since the start of the treatment?
Did you notice that your hairs felt more healthy during the past month?
Did you notice that your hairs felt more healthy since the start of the treatment?
The tenth and eleventh questions asked whether hairs felt less fragile during the past month and since the start of the treatment.
The final questions asked whether participants had noticed their hair color increasing and whether it became less grey/white during the past month and since the start of the treatment.

Figure 3:
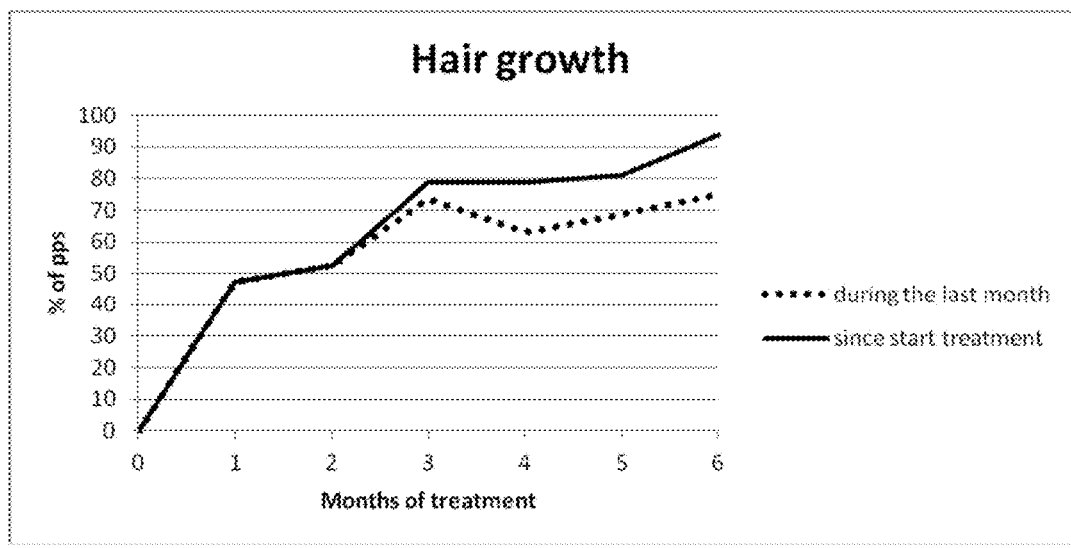
FIG. 3 shows a chart of self-reported increases in participants' ("pps") hair growth during the last, prior month following treatment with the compound of Formula (I) (dotted line) and since the start of treatment (solid line).

FIG. 3 shows data for noticeable hair growth, both for hair growth during the past month (dotted line, "last month") and since the start of treatment (solid line). After 1 month of treatment 47% of participants noticed new hair growth. After 6 months of treatment, 94% of participants noticed new hair growth.

Figure 4:
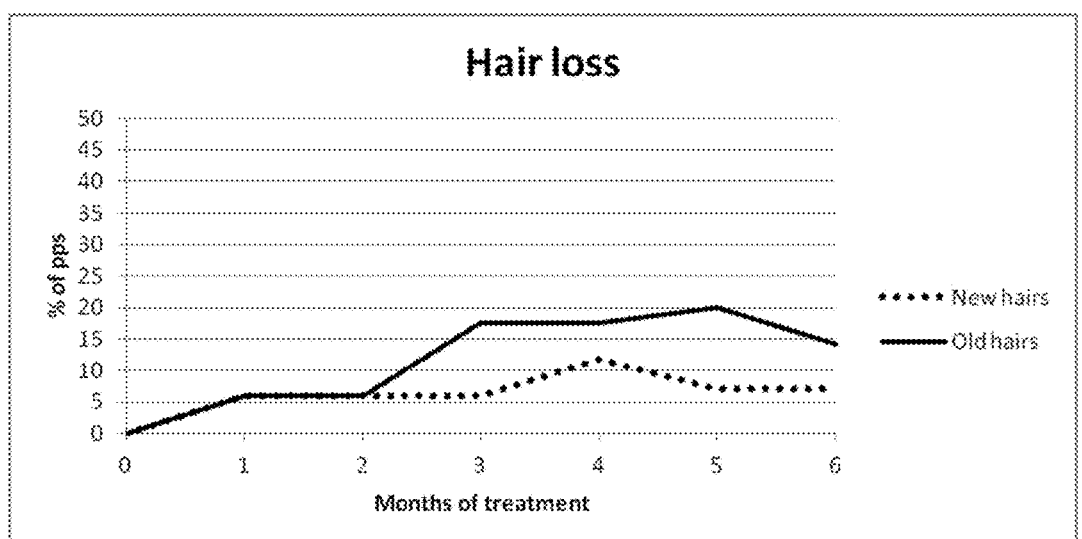
FIG. 4 shows a chart of self-reported loss of new hairs (dotted line) and old hairs (solid line) over the course of treatment with the compound of Formula (I).

FIG. 4 shows data for any hair loss that participants noticed since the start of the treatment. Over the whole course of the treatment, 14% of participants noticed that some new hairs fell out. At some point during treatment, 20% of participants indicated that they noticed an increase in hair loss. However, additional questions indicated that participants felt that this hair loss was due to more healthy hair taking the place of old, fragile hair. (Note that data obtained from the two alopecia patients were not collected for the hair loss questions, nor for any of the following questions, except as indicated below.)

Figure 5:
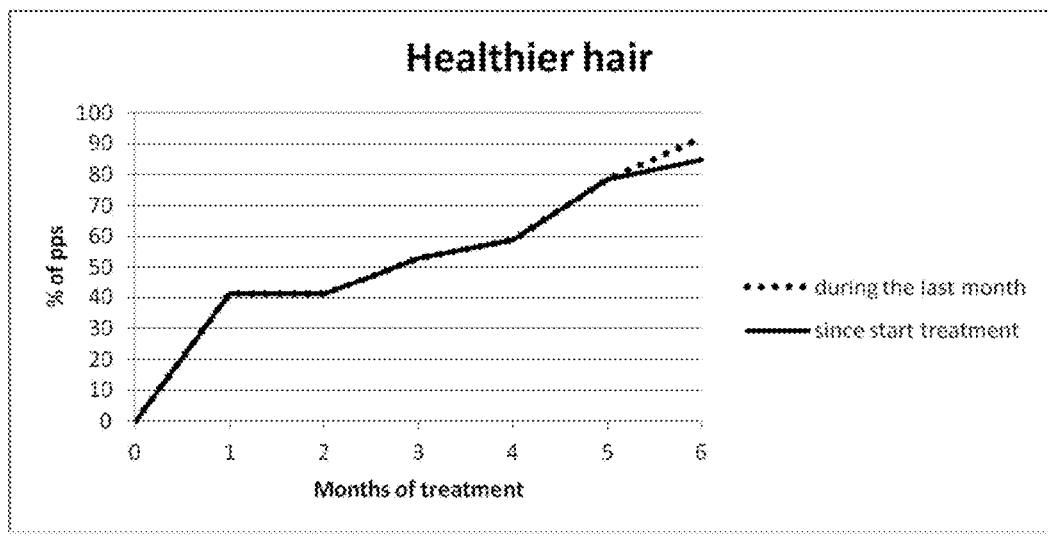
FIG. 5 shows a chart of self-reported improvements in the health of participants' hair during the last, prior month (dotted line) and since the start of treatment (solid line) with the compound of Formula (I).

In regard to hair health, all participants provided similar answers that suggest that they felt their hair became healthier, thicker, and less fragile. As shown in FIG. 5, approximately 85-92% of participants had noticed an increase in healthy hair, thicker hair and less fragile hair during the last month of treatment (dotted line) since the start of treatment (solid line).

Figure 6:
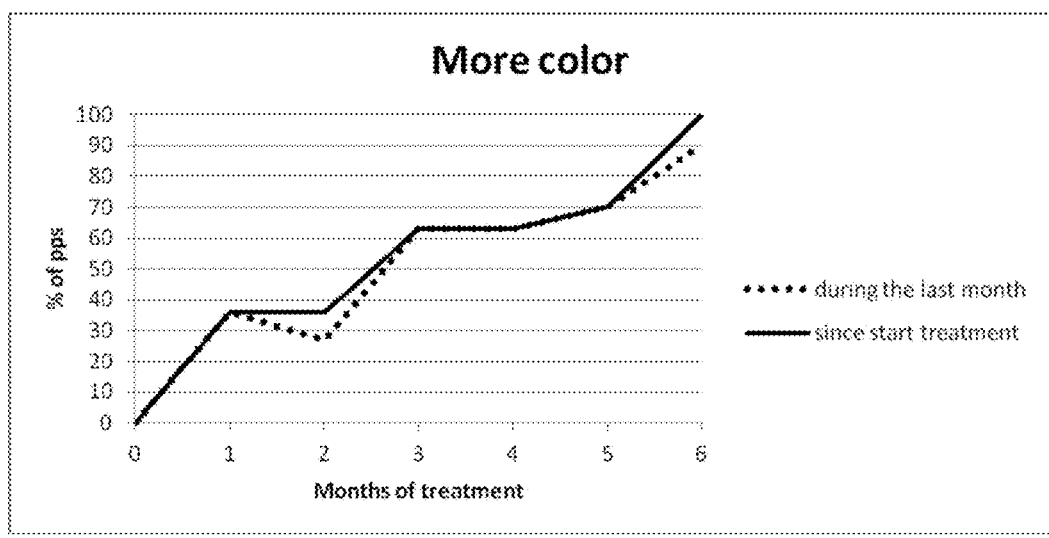
FIG. 6 shows a chart of self-reported increases in hair color in white/gray haired participants during the last, prior month (dotted line) and since the start of treatment (solid line) with the compound of Formula (I).

In regard to hair color, FIG. 6 shows that participants who had white/grey hair before the start of the treatment reported that they noticed a significant increase in color during the last month of treatment (dotted line) and since the start of treatment (solid line).

For each participant one specific place was chosen for hair growth by digital analysis of photographs. Typically, a bald spot or a spot with thinning hair was selected for photographic analysis. Hair growth was measured by counting and estimating the total amount of thick/thin hairs on the specific spot, based on digital analysis of each photograph.

Figure 7:
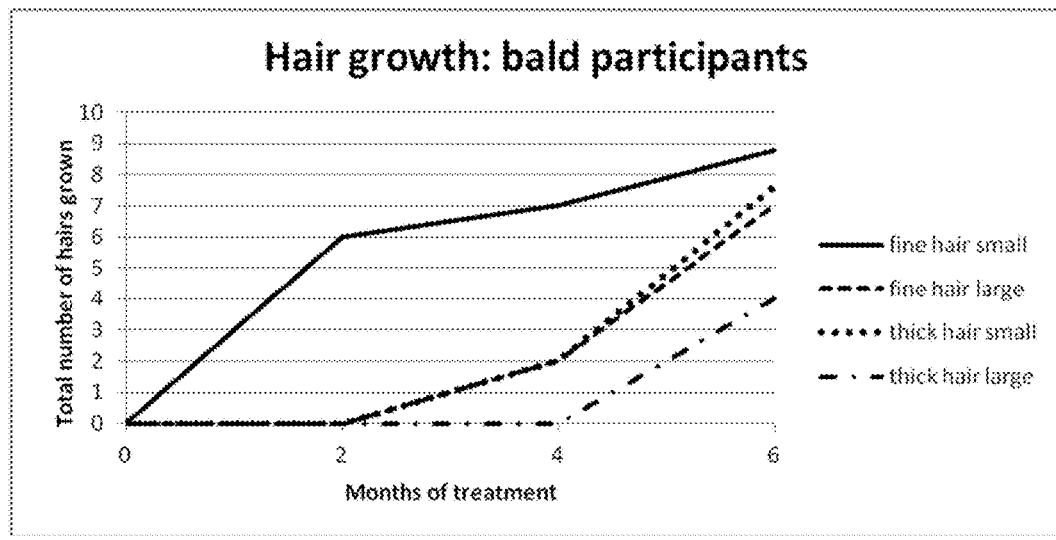
FIG. 7 shows a chart of increases in different hair types in bald participants over the course of treatment with the compound of Formula (I) measured by photo analysis.

FIG. 7 shows the data of bald participants, including alopecia patient data. On average, the data provide clear evidence that both fine hairs and more thick hairs suddenly started to grow for participants who initially had no hair at the probed place.

Figure 8:
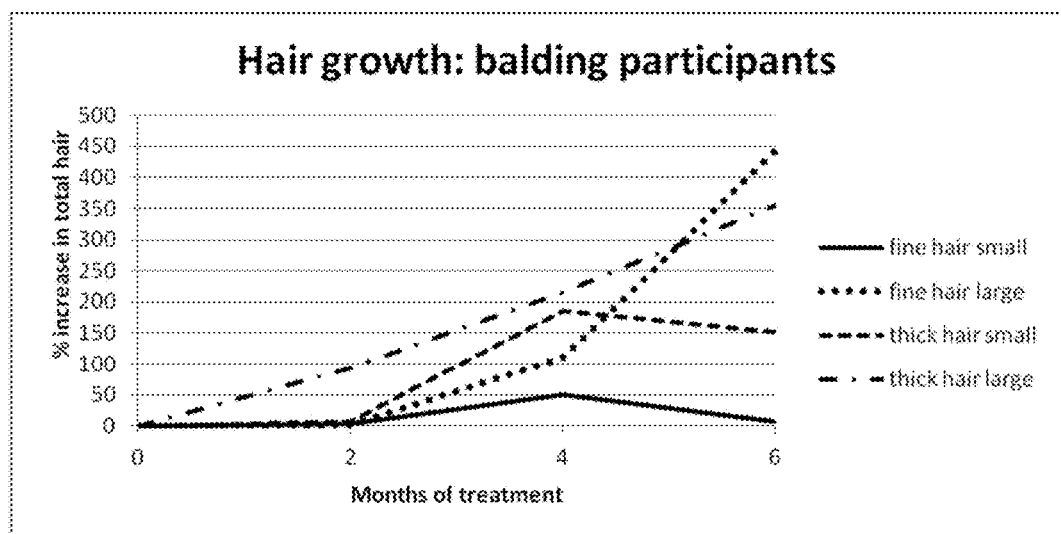
FIG. 8 shows a chart of increases in different hair types in balding participants over the course of treatment with the compound of Formula (I) measured by photo analysis.

FIG. 8 shows the data of balding participants, which clearly shows a remarkable increase in hair growth (% increase in total hair of each thickness type). After 6 months, triple to quadruple overall increases in both long fine and thick hairs were observed.

Figure 9:
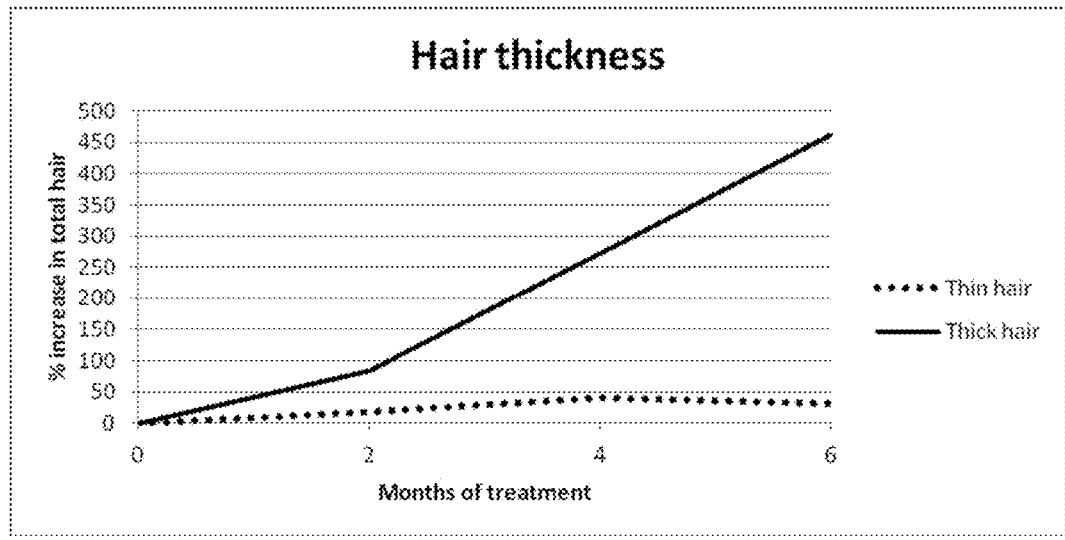
FIG. 9 shows a chart of self-reported increases in hair thickness over the course of treatment with the compound of Formula (I).

FIG. 9 shows that participants with thin hair exhibited a significant increase in the amount of thick hair.

Figure 10:
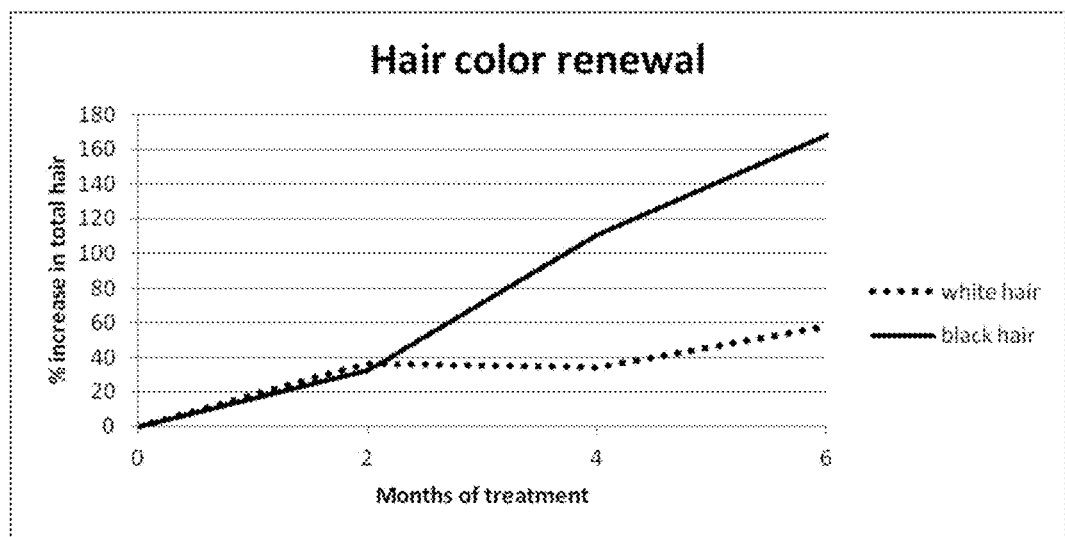
FIG. 10 shows a chart of self-reported increases in white and black hair over the course of treatment with the compound of Formula (I).

As shown in FIG. 10, the questionnaires revealed that participants with white/grey hair clearly observed an increase in the percent of total hair that was black, whereas the amount of white hair increased to a lesser extent.

The data obtained via questionnaires and photo analyses provide clear evidence that the composition containing the compound of Formula (I) is highly effective in stimulating hair growth. Data suggest that application of the composition containing the compound of Formula (I) to the scalp leads to a significant increase in total amount of hairs, even in participants who had no hair and in participants who have clinical alopecia totalis. Moreover, these results suggest that the formula is potent at reviving the hair, leading to thicker and healthier hair as well as hair having the participant's original hair color. Overall these results suggest regeneration of the hair and cells involved in the hair growth cycle.

However, some individual variance in treatment effects was apparent. That is, not all participants showed the same increase in hair growth and hair health. Though this could be the result of a number of different factors, the inventors put forth the non-limiting hypothesis that stress factors and nutritional factors are likely involved in the observed differences.

Figure 11A:
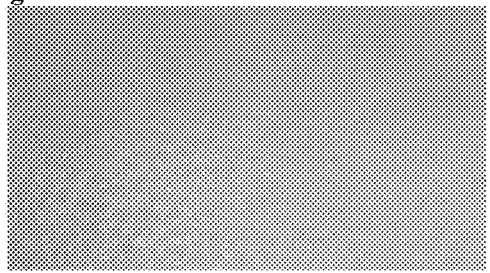
FIG. 11A shows a close-up of alopecia at the top of a female subject's head who lost all head and body hair after trauma.
Figure 11B:
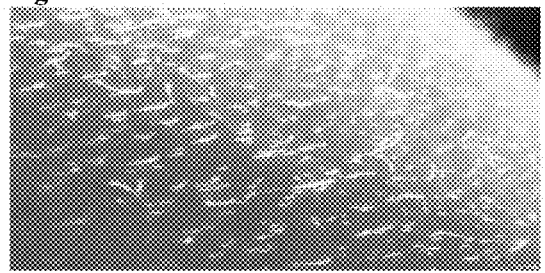
FIG. 11B shows hair growth at the alopecia site on the subject from FIG. 11A after 4 months of treatment with the compound of formula (I).
Figure 11C:
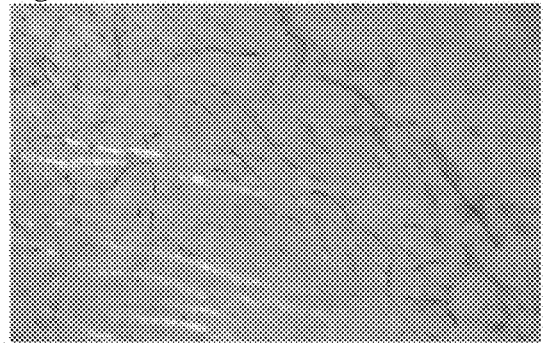
FIG. 11C shows the hair growth from FIG. 11B after the fine, white hair growth was treated with hair color to enhance the visibility.

FIG. 11 shows hair regrowth at an injured site before and after treatment with Formula (I). FIG. 11A shows a close-up of alopecia at the top of a female subject's head who lost all body hair after trauma. FIG. 11B shows hair growth at the alopecia site on the subject from FIG. 11A after 4 months of treatment with the compound of Formula (I). FIG. 11C shows the hair growth from FIG. 11B after the fine, white hair growth was treated with hair color to enhance visibility.

Along these lines, a lab technician who burned both hands, and hair regrowth at the site of the burn was assessed. One hand was treated for one month with a composition comprising Formula (I), and the other hand was left untreated. After one month the hand treated with Formula (I) developed new smooth skin. The untreated hand developed calluses instead.

Therefore, it should be appreciated that the compounds for hair regrowth produced by the methods described herein, may be also be used to prevent or treat skin at an injured site on a mammal/human. As used herein, "injured site" includes a burn site (including burns caused by cold, heat, or chemicals), bruises, abrasions, cuts, or compromised due to age related degeneration. Thus, the skin at the injured site may be intact and not bleeding. As such, one having ordinary skill in the art appreciates that the inventive methods, compounds, topical formulations, and methods of treatment may improve wound healing, especially by stimulating hair regrowth at injured sites that would form hairless scar tissue if left untreated.

Although some embodiments of the inventive topical compositions are described herein as comprising Formula (I), the inventors contemplate that any reaction component alone or in combination may stimulate hair regrowth.

In yet further aspects of the inventive subject matter, cosmetic collagen regeneration effects of Formula (I) were assessed in a clinical trial run by Sempervivum, a medical esthetics company. Twenty-four volunteers (22 women and 2 men) participated in this study. Participants were on average 59 years old (Mean (M)=59 years, Standard Deviation (SD)=12 years). In this case, the age of the participants is 59 years with an average deviation of 12 years.

Figure 12A:
FIG. 12A shows a high-resolution ultrasound scanner image of a skin structure suffering from photo ageing that has disorganized collagen appears as dark areas in the upper dermis.
Figure 12B:
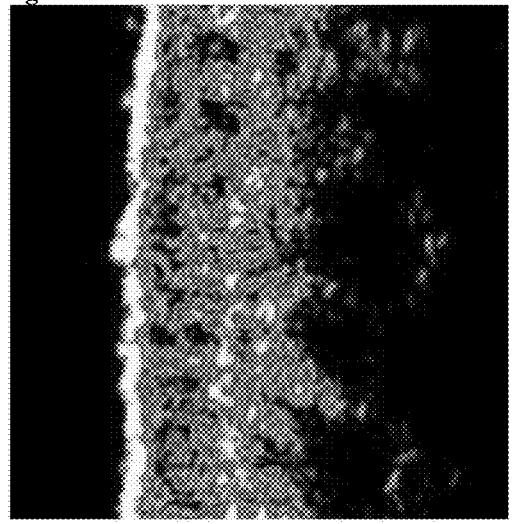
FIG. 12B shows a high-resolution ultrasound scanner of a skin structure treated with a compound produced by the inventive methods, wherein the collagen matrix has an increased density, and the skin has a smoother surface.

Participants had no history of cosmetic surgery and stated to have normal eating and sleeping patterns. High-resolution ultrasound scanner images of collagen in sun damaged skin are shown in FIG. 12A (before treatment) and FIG. 12B (after treatment). The images taken after treatment show significant increases in collagen. It also appears that more interconnected collagen fibers are present in the dermis of the skin, and spots representing collagen seem to be more connected and closer to the epidermal layer.

Hair growth was also assessed for an 85-year-old participant of the collagen study who was suffering from thinning hair. The participant applied the topical composition (cream) at the base of the scalp on her forehead for 6 months. Subsequent analysis showed the return of healthy and thick hair after only 3 months.

Additionally, the enzyme 5-alpha-reductase converts testosterone into dihydrotestosterone (DHT). DHT in involved in the shrinking of hair follicles, causing thinning hair. In contrast, when DHT levels are suppressed, hair follicles continue to thrive. Men in the collagen study with hair thinning caused by elevated DHT applied a spray of the products of the inventive methods to the thinning area of the back of the scalp for 2 months. After which, hair started to grow thicker and more abundant after 2 months.

The preceding discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

What is claimed is:

1. A method of producing a composition for hair regrowth, wherein the composition comprises a compound having a structure according to Formula (I)

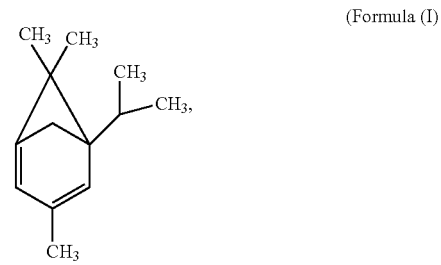

(Formula (I))

the method comprising:
  (1) adding a Friedel-Crafts catalyst to a 1,2-dichloroalkane to generate a first intermediate at a first temperature, wherein the first temperature is between −10 and 15 degrees Celsius, inclusive
  (2) adding the first intermediate to an alkylbenzene at the first temperature and to generate a second intermediate;
  (3) cooling the second intermediate to a second temperature to generate a third intermediate, wherein the second temperature is between −90 and −70 degrees Celsius, inclusive;
  (4) incubating the third intermediate at the second temperature for a first duration;
  (5) warming the third intermediate to a third temperature and incubating the third intermediate at the third temperature for a second duration, wherein the third temperature is between 30 and 50 degrees Celsius, inclusive;
  (6) cooling the third intermediate to the second temperature and incubating the third intermediate at the second temperature for a third duration; and
  (7) repeating steps (5) and (6) at least four times.

2. The method of claim 1, wherein the Friedel-Crafts catalyst comprises aluminum trichloride or ferric chloride.

3. The method of claim 1, wherein the 1,2-dichloroalkane comprises a 1,2-dichloropropane.

4. The method of claim 1, wherein the alkylbenzene comprises toluene.

5. The method of claim 1, wherein the first temperature is about 4 degrees Celsius.

6. The method of claim 1, wherein the first, second, and third duration are about 30 minutes.

7. A topical formulation for stimulating hair regrowth comprising a composition produced by the method of claim 1 and a carrier, wherein the 1,2-dichloroalkane is 1,2-dichloropropane, and wherein the alkylbenzene is toluene.

8. The topical formulation of claim 7, wherein the carrier comprises a cream, a lotion, an ointment, or a spray.

9. The topical formulation of claim 7, wherein the carrier comprises a foam or a gel.

10. The topical formulation of claim 7, wherein the composition is encapsulated in a micelle or liposome.

11. The topical formulation of claim 7, wherein the composition is encapsulated in a polymeric bead.

12. A method of stimulating hair regrowth comprising: providing a topical formulation of claim 7 in an amount effective to stimulate at least one of:
   i) activating the anagen phase in a hair follicle;
   ii) inhibiting the hair follicle from entering the catagen phase;
   iii) reverting the hair follicle from the catagen phase to the anagen phase; and
   iv) promoting the hair follicle to enter the anagen phase from the telogen phase; and
      applying the topical formulation to a treatment area of a human in need thereof.

13. The method of claim 12, wherein the amount is further effective to stimulate expression of Lgr5 in a follicular stem cell in the treatment area of the human in need thereof.

14. The method of claim 12, wherein the treatment area comprises an injured site on the human in need thereof.

15. The method of claim 14, wherein the injured site on the human in need thereof comprises a burn.

16. The method of claim 12, wherein the amount is further effective to stimulate an increase in collagen and elastin levels in the skin of a human in need thereof.

17. A method of increasing collagen and elastin levels in the skin of a human in need thereof comprising providing the topical formulation of claim 7 and applying the topical formulation to a treatment area of a human in need thereof.

* * * * *